United States Patent
Soltani-Ahmadi et al.

[11] Patent Number: 5,493,035
[45] Date of Patent: Feb. 20, 1996

[54] PROPYLENE OXIDE PURIFICATION

[75] Inventors: Ahmad Soltani-Ahmadi, Radnor; Thomas C. Mullin, Exton, both of Pa.

[73] Assignee: Arco Chemical Technology, L.P., Greenville, Del.

[21] Appl. No.: 410,164

[22] Filed: Mar. 24, 1995

[51] Int. Cl.$^6$ .................. C07D 301/32; C07D 303/04
[52] U.S. Cl. ............... 549/542; 568/867; 588/218
[58] Field of Search ............................................ 549/542

[56] References Cited

U.S. PATENT DOCUMENTS

| | | |
|---|---|---|
| 4,692,535 | 9/1987 | Larson et al. |
| 4,831,196 | 5/1989 | Buonicore et al. ............ 549/542 |
| 5,187,287 | 2/1993 | Shih . |
| 5,352,807 | 10/1994 | Shih . |

Primary Examiner—Joseph E. Evans
Attorney, Agent, or Firm—William C. Long

[57] ABSTRACT

Activated carbon to be used in the removal of impurities from propylene oxide is first pre-wetted with a glycol such as propylene glycol; after bed deactivation, water containing a basic catalyst is added to hydrolyze propylene oxide and to form a non-hazardous slurry of carbon, propylene glycol and water.

7 Claims, 4 Drawing Sheets

PROPYLENE OXIDE PURIFICATION

BACKGROUND OF THE INVENTION

1. Field of the Invention

The present invention relates to the purification of alkylene oxides such as propylene oxide by contact with solid activated carbon adsorbent and especially to a process wherein the activated carbon is first contacted and prewetted with a glycol such as propylene glycol before contact with the alkylene oxide whereby excessive exotherms caused by the heat of adsorption are substantially avoided; in addition, a substantially improved carbon bed changeover procedure is provided.

2. Description of the Prior Art

Methods are known in the art for the purification of alkylene oxides such as propylene oxide by contact with solid activated carbon.

U.S. Pat. No. 4,692,535, for example, shows separation of high molecular weight poly (propylene oxide) polymer from propylene oxide by contact with activated carbon.

U.S. Pat. No. 5,187,287 and related U.S. Pat. No. 5,352,807 show the separation of various organic impurities from lower alkylene oxides such as propylene oxide and butylene oxide by activated carbon treatment.

There are various difficulties associated with the treatment of propylene oxide with activated carbon. Due to the considerable heat released upon adsorption of propylene oxide on activated carbon there are both hazards and possible damage to the carbon bed associated with excessive temperature increases during the initial or start-up phase of the activated carbon treatment process. Where the bed is contacted with liquid propylene oxide, the accompanying adsorption exotherm has resulted in propylene oxide vaporization and migration in the bed which in turn causes secondary exotherms with temperatures in excess of 500° C. with extreme hazard and reactor damage. During bed changeover, a major concern has been the handling of toxic and hazardous carbon/propylene oxide/water slurries which pose safety and environmental hazards.

Prior carbon treatment procedures have required vapor recovery systems, the provision of steam, nitrogen, cooling, flare facilities as well as sophisticated control systems and trained operators.

Difficulties are compounded by the fact that high molecular weight poly (propylene oxide) polymer can be formed during shipping and storage of propylene oxide and this polymer formation has a pronounced adverse effect on the use of polyols formed from the propylene oxide in polyurethane foams. U.S. Pat. No. 4,692,535 provides a detailed description of this. Although propylene oxide can be purified at the source, impurities form during shipping and storage, and frequently it has not been practical to provide the sophisticated facilities and operation at various locations where the propylene oxide is used to accomplish activated carbon treatment by prior procedures.

SUMMARY OF THE INVENTION

In accordance with the present invention, activated carbon which is to be used to treat propylene oxide is first contacted with a glycol such as propylene glycol, usually in amount of at least 1 lb. of propylene glycol per 5 lbs. of carbon. Although there is an adsorption exotherm associated with glycol adsorption on the carbon, this does not pose any particular problems in view of the relatively high boiling and flash points of the glycols. Indeed, the activated carbon can be prewetted with glycol before shipping to the site where it is to be used and can be charged to the treatment vessel in the prewetted condition. The activated carbon containing adsorbed glycol is then contacted with propylene oxide which is to be purified in accordance with standard procedures. During this contact, there is an initial period during which the propylene oxide displaces the adsorbed glycol, after which purification of the propylene oxide takes place normally. An important feature is that there is little or no exotherm accompanying the displacement of glycol and purification of the propylene oxide thus resulting in a much easier and safer operation. Little or no utilities or sophisticated control systems are needed, and the procedure is well adapted for use at the location where the propylene oxide is to be used, for example, in the formation of polyols for polyurethane foam.

DETAILED DESCRIPTION

In accordance with the present invention, activated carbon, which is to be used for the removal of impurities from propylene oxide, is first contacted with sufficient glycol to substantially saturate the active carbon. Preferably the activated carbon is wetted with liquid propylene glycol in an amount of at least 1 lb. propylene glycol per 5 lbs. carbon, preferably at least 1 lb. propylene glycol per 3 lbs. carbon. Good results are obtained where at least 1 lb. propylene glycol per 2 lbs carbon is used and there appears to be no advantage to using greater amounts of glycol although greater amounts can be used if desired.

After contact with glycol, the activated carbon containing adsorbed glycol can be cooled to remove the exotherm associated with glycol adsorption; alternatively the carbon can be pre-sprayed with the glycol prior to being charged to the vessel in which the contact takes place. The glycol containing carbon is then contacted with sufficient propylene oxide, preferably as liquid, to displace the adsorbed glycol without a substantial exotherm. During the displacement period, a mixture of propylene oxide and displaced glycol is collected, which mixture can be conveniently converted to all glycol by suitable hydrolysis procedures or sent to a refiner or to a polyol production operation.

After displacement of the glycol, the activated carbon is used in a normal fashion for the removal of impurities from propylene oxide as described in U.S. Pat. Nos. 4,692,535 and 5,352,807, for example. The impurities removal capability of the carbon is not adversely affected by the glycol pre-saturation.

When the impurities removal capability of the carbon has decreased to an uneconomical degree, carbon bed changeover is conveniently carried out by draining free liquid propylene oxide from the carbon bed and then converting residual propylene oxide to propylene glycol by addition of water containing a catalytic amount of a base such as NaOH. The resulting slurry of carbon/water/propylene glycol is non-hazardous and can be pumped to a tank truck for disposal.

A series of experiments were conducted to illustrate the advantages of the present invention. In each case about 750 grams of activated carbon, Calgon 12×40, were placed in a cylinder 4" in diameter and 8" long. Means were provided for the introduction of propylene oxide and nitrogen vapor mixtures or liquid propylene glycol into the carbon bed and for removal therefrom. Thermocouples were placed at the inlet, at points 0.25", 4" and 7.75" into the bed and at the bed outlet along the cylinder axis in order to provide a temperature profile for each case. The outer skin temperature of the cylinder was also measured.

Figure 1:
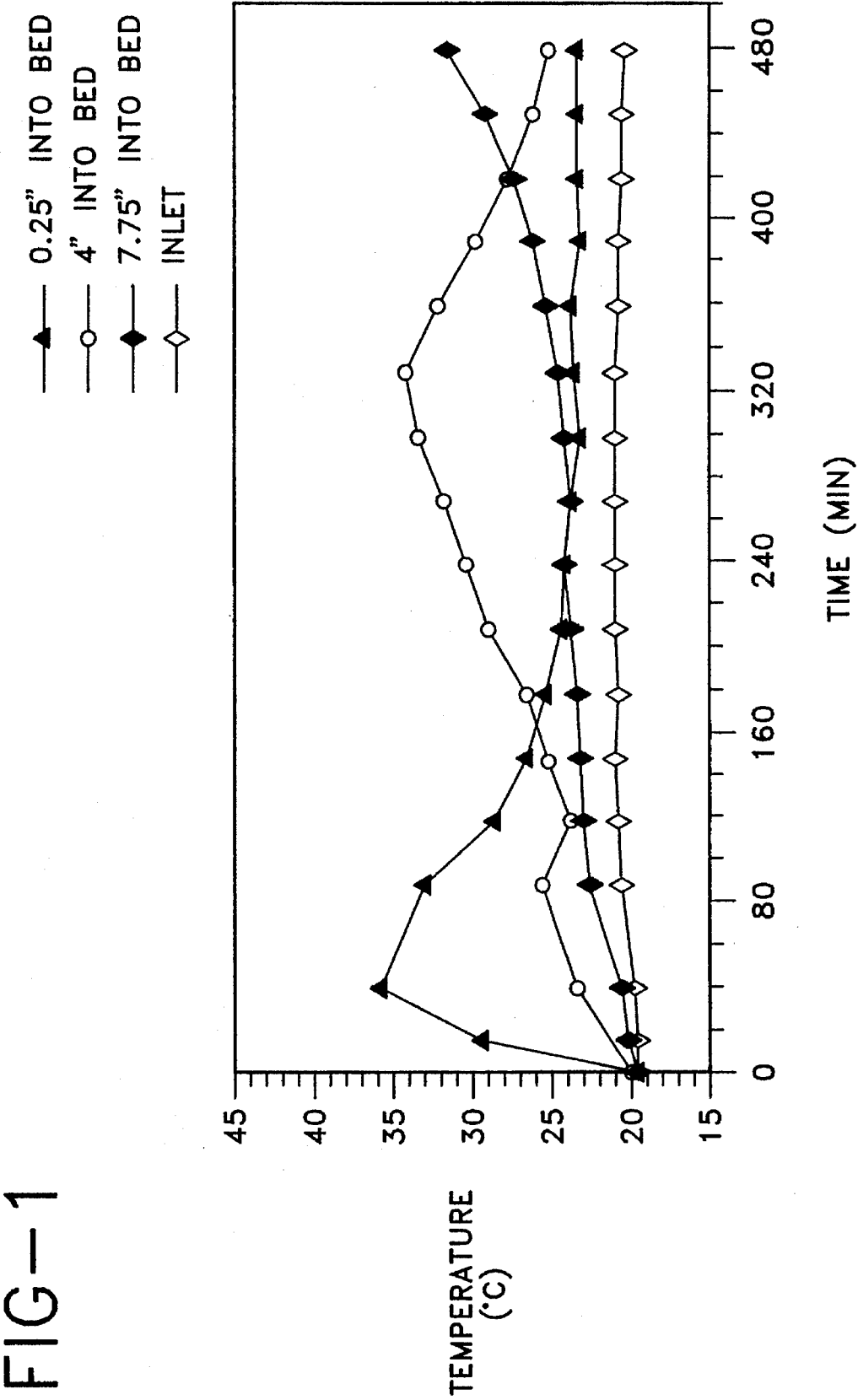
FIG. 1 is a plot of temperature versus time which results during conventional procedures involving saturation of activated carbon with a 10 wt % vapor mixture of propylene oxide in nitrogen.

In a first comparative run illustrating current practices, a vapor mixture of 10 wt % propylene oxide in nitrogen was charged to the carbon bed at the rate of 133 grams/min propylene oxide. Attached FIG. 1 shows the resulting temperature profile. As can be seen, there was a modest exotherm but the procedure required in excess of 500 minutes and in commercial use requires sophisticated controls in order to avoid potential hazards.

It should be noted that in practices such as illustrated in FIG. 1, protection must be provided in case of loss of nitrogen flow. In such a case, temperature spikes within the carbon bed occur which require external cooling and shut down of the unit. In some instances where liquid propylene oxide has been introduced to the carbon bed there have been temperature spikes of 160° C. or more which in turn lead to vaporization and migration of propylene oxide which leads to a second exotherm with temperature spikes of 500° C. or more. In such extreme cases, reactor damage can occur and the danger of fire and explosion exists.

Figure 2:
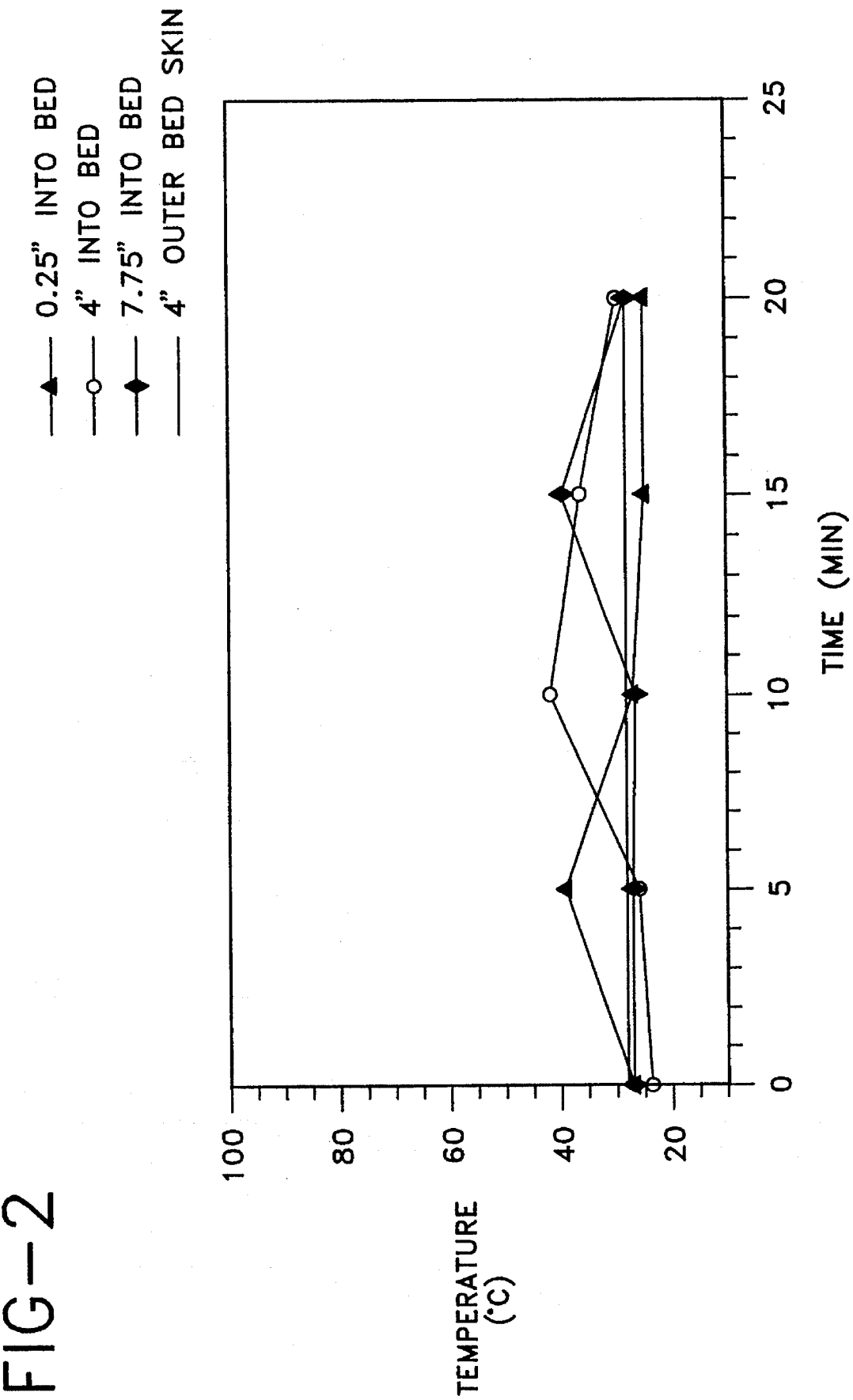
FIG. 2 is a plot of temperature versus time resulting from the activated carbon treatment of liquid oxide wherein the carbon had first been prewetted with 20 wt % propylene glycol.

In a series of experiments in accordance with the invention, the carbon bed was first pre-wet with liquid propylene glycol and subsequently liquid propylene oxide was charged to the carbon bed at the rate of 133 grams/min. FIG. 2 shows the bed temperature profile where the amount of propylene glycol used to pre-wet the bed was 20% by weight of the carbon contained in the bed. As can be seen there was a slight exotherm resulting in temperatures reaching only about 40° C., far less than the maximum which can result where there is no propylene glycol pre-addition.

Figure 3:
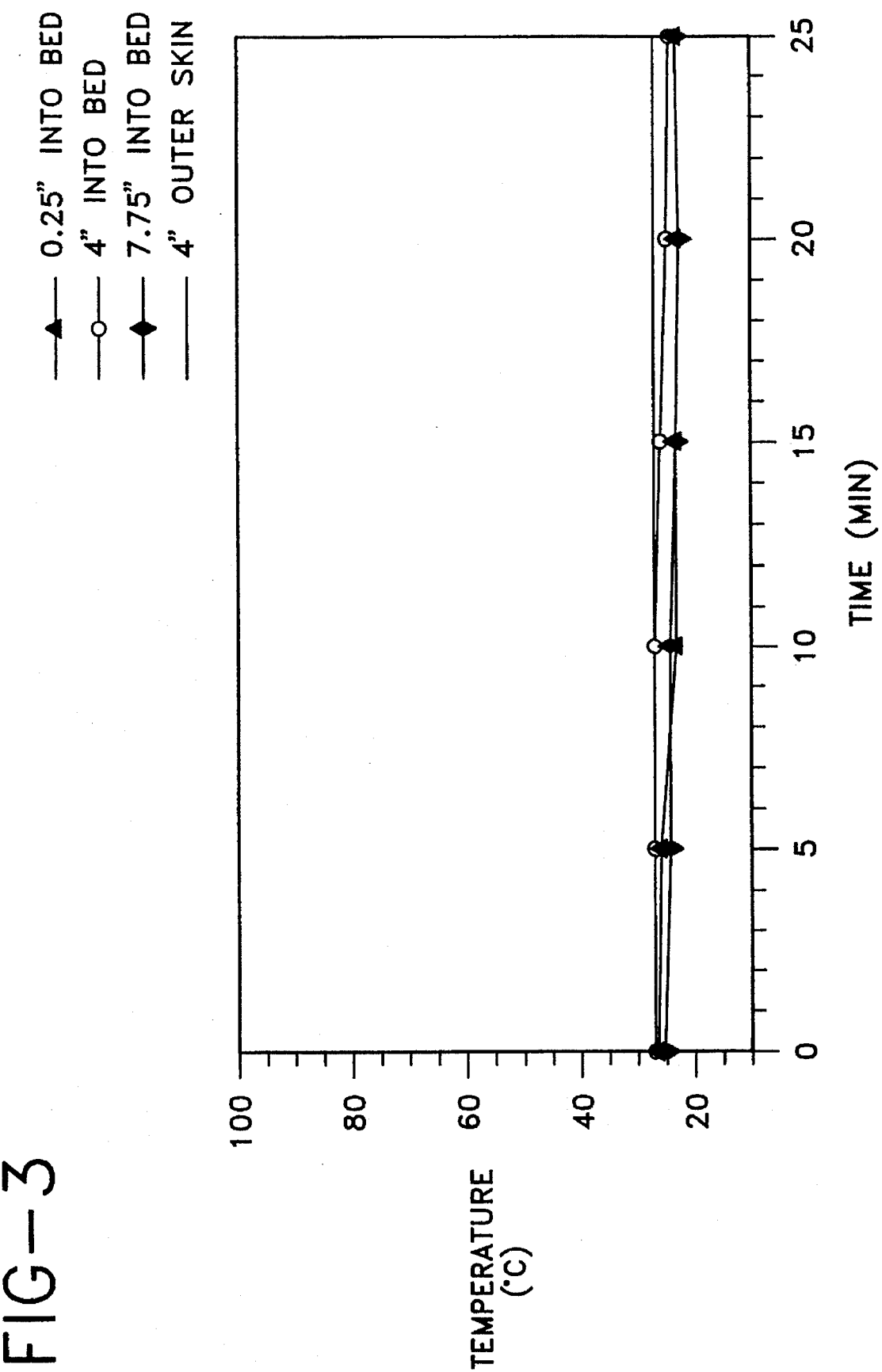
FIG. 3 is a plot of the exotherm which results from the activated carbon treatment of liquid propylene oxide wherein 33.3 wt % propylene glycol had first been used to pre-saturate the carbon.

FIG. 3 shows the bed temperature profile where the amount of propylene glycol used to pre-wet the bed was 33.3% by weight of the carbon contained in the bed. As can be seen, there was essentially no bed temperature increase due to an adsorption exotherm.

Figure 4:
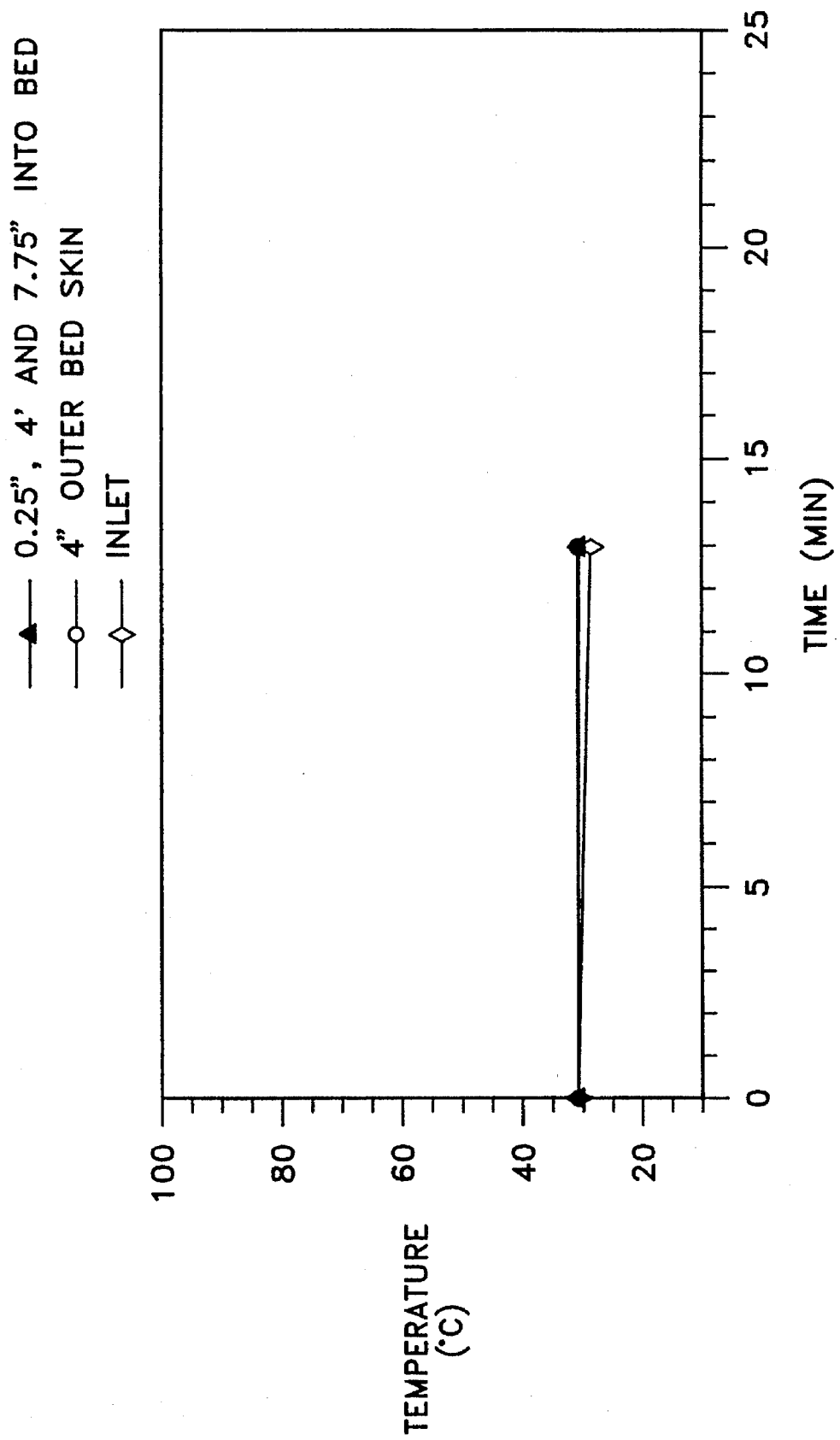
FIG. 4 is a plot of the exotherm which results from the activated carbon treatment of liquid propylene oxide wherein 50 wt % propylene glycol had first been used to pre-saturate the carbon.

FIG. 4 shows the bed temperature profile where the amount of propylene glycol used to pre-wet the bed was 50% by weight of the carbon contained in the bed. Again, there was essentially no bed temperature increase.

In order to determine whether the carbon pre-wetted with propylene glycol retained its ability to remove impurities from propylene oxide, inlet and outlet propylene oxide samples were taken after 15 gallons of propylene oxide had passed through the bed. The following table shows the inlet and outlet concentrations of poly (propylene oxide) of different molecular weight.

TABLE 1

| | Poly (Propylene Oxide) | | | |
|---|---|---|---|---|
| | Mol wt. above 30,000 | | Mol wt. above 450,000 | |
| | Inlet (ppm) | Outlet (ppm) | Inlet (ppm) | Outlet (ppm) |
| Run 1 | 1.09 | 0.13 | 0.13 | 0.00 |
| Run 2 | 1.84 | 0.14 | 0.32 | 0.00 |
| Run 3 | 1.69 | 0.10 | 0.18 | 0.00 |

For Run 1, the carbon bed had been pre-saturated by passage of a gas mixture of 10 wt % propylene oxide in nitrogen through the bed. For Run 2, the carbon bed had been pre-saturated by passage of a gas mixture of 72 wt % propylene oxide in nitrogen through the bed. For Run 3, the carbon had been was pre-saturated with 33.3% liquid propylene glycol based on the weight of carbon. In each case, after pre-saturation liquid propylene oxide was introduced at the rate of 133 grams/min and the samples were taken for analysis after 15 gallons of propylene oxide had been processed.

The data clearly establish that pre-saturation with propylene glycol did not adversely affect the impurities removal capability of the activated carbon.

As a further feature of the invention, after the effectiveness of an activated carbon bed has declined to an unsatisfactory level, a changeover of the carbon bed is accomplished, after draining free propylene oxide, by the addition of water containing a catalytic amount of NaOH or other basic material, e.g. KOH, whereby residual propylene oxide is converted to propylene glycol. The resulting admixture of water, carbon and propylene glycol can be conveniently transported to disposal. In this aspect of the invention, water containing basic catalyst is contacted with the propylene oxide saturated carbon in at least amount sufficient to hydrolyze all of the adsorbed propylene oxide. Normal temperatures are effective for the hydrolysis, and after sufficient reaction time, e.g. 10 minutes to 4 days, the resulting non-hazardous slurry of carbon, propylene glycol and water can be removed as by pumping for disposal.

The activated carbon and propylene oxide treatment conditions used herein are as described in U.S. Pat. Nos. 5,352,807 and 4,692,535, the disclosures of which are incorporated by reference.

In practice of the invention, the use of propylene glycol is greatly preferred. Glycols generally can be used, especially those having 2 to 4 carbon atoms such as ethylene glycol, 2,3-butylene glycol, and the like with similar effectiveness. Also included in the definition of glycols used herein are glycols which have been oxyalkylated with ethylene oxide and/or propylene oxide.

I claim:

1. In a process for the removal of impurities from propylene oxide by contact with activated carbon, the improvement which comprises pre-wetting the activated carbon with a glycol prior to the contact with propylene oxide.

2. The process of claim 1 wherein the glycol is propylene glycol.

3. The process of claim 1 wherein the glycol is ethylene glycol.

4. The process of claim 1 wherein the carbon bed is pre-wetted with at least 20 wt % propylene glycol based on the weight of carbon.

5. The process of claim 1 wherein the carbon bed is pre-wetted with at least 33.3 wt % propylene glycol based on the weight of carbon.

6. The process of claim i wherein the carbon bed is pre-wetted with at least 50 wt % propylene glycol based on the weight of carbon.

7. The process of claim 1 wherein after the activated carbon has deactivated to a predetermined extent, the carbon is contacted with water containing a basic catalyst and adsorbed propylene oxide is hydrolyzed to propylene glycol.

\* \* \* \* \*